United States Patent
Hubbard et al.

(10) Patent No.: US 10,869,648 B2
(45) Date of Patent: Dec. 22, 2020

(54) DEVICE, SYSTEM AND METHOD FOR FLOW IMAGING IN THE BODY USING A SWEPT TRANSDUCER

(71) Applicant: Volcano Corporation, San Diego, CA (US)

(72) Inventors: Frank Hubbard, San Francisco, CA (US); Dietrich Ho, Mountain View, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 435 days.

(21) Appl. No.: 13/892,081

(22) Filed: May 10, 2013

(65) Prior Publication Data

US 2013/0303910 A1    Nov. 14, 2013

Related U.S. Application Data

(60) Provisional application No. 61/646,083, filed on May 11, 2012.

(51) Int. Cl.
*A61B 8/06* (2006.01)
*A61B 8/12* (2006.01)
*A61B 8/00* (2006.01)

(52) U.S. Cl.
CPC .................. *A61B 8/06* (2013.01); *A61B 8/12* (2013.01); *A61B 8/4209* (2013.01); *A61B 8/445* (2013.01); *A61B 8/4461* (2013.01)

(58) Field of Classification Search
CPC ........... A61B 8/06; A61B 8/4209; A61B 8/12; A61B 8/4461; A61B 8/445
USPC ....................................................... 600/443
See application file for complete search history.

(56) References Cited

U.S. PATENT DOCUMENTS

| 5,379,772 | A |   | 1/1995 | Imran |
| 5,685,308 | A | * | 11/1997 | Wright ............... G01S 7/52023 600/443 |
| 6,110,118 | A | * | 8/2000 | Guracar et al. ............... 600/453 |

(Continued)

FOREIGN PATENT DOCUMENTS

| JP | 2003-130699 | 5/2003 |
| WO | WO 2009140641 A2 * | 11/2009 ............... A61B 8/12 |

OTHER PUBLICATIONS

Diethrich et al. Virtual histology and color flow intravascular ultrasound in peripheral interventions. 2006 Semin.Vasc.Surg. 19:155-162.*

(Continued)

*Primary Examiner* — Keith M Raymond
*Assistant Examiner* — Patrick M Mehl

(57) ABSTRACT

An ultrasound imaging system is disclosed. The system comprises an ultrasound emitter and receiver movably disposed within an elongate member, an actuator coupled to the emitter, and a control system. The actuator moves the emitter through a path comprising at least a portion of an arc. The control system controls the emission of a sequence of pulses from the emitter and receives from the receiver ultrasound echo data associated with the sequence of pulses emitted along the path. The control system processes the ultrasound echo data to generate a cross-sectional image of an internal structure based on echo amplitude data and echo velocity data.

12 Claims, 8 Drawing Sheets

(56) References Cited

U.S. PATENT DOCUMENTS

| | | | |
|---|---|---|---|
| 6,241,677 B1* | 6/2001 | Guracar | A61B 8/08 600/453 |
| 2002/0062086 A1* | 5/2002 | Miele | A61B 5/02028 600/483 |
| 2005/0043614 A1* | 2/2005 | Huizenga | A61B 5/055 600/427 |
| 2005/0228280 A1* | 10/2005 | Ustuner | A61B 8/06 600/443 |
| 2006/0149330 A1 | 7/2006 | Mann et al. | |
| 2007/0016062 A1* | 1/2007 | Park et al. | 600/459 |
| 2007/0016072 A1* | 1/2007 | Grunwald | A61B 5/06 600/468 |
| 2008/0177138 A1* | 7/2008 | Courtney | A61B 5/0062 600/109 |
| 2009/0264768 A1 | 10/2009 | Courtney et al. | |
| 2011/0005322 A1* | 1/2011 | Ustuner | G01N 29/069 73/627 |
| 2011/0218437 A1 | 9/2011 | Park et al. | |
| 2012/0123271 A1* | 5/2012 | Cai | A61B 8/06 600/454 |

OTHER PUBLICATIONS

Garcia-Garcia et al. IVUS-based imaging modalities for tissue characterization similarities and differences. 2011 J. Cardiovasc. Imaging 27:215-224.*

Ge et al. Comparison of intravascular ultrasound and angiography in the assessment of myocardial bridging. 1994 Circulation 89:1725-1732.*

Hasegawa et al. Simultaneous Imaging of Artery-Wall Strain and Blood Flow by High Frame Rate Acquisition of RF Signals. 2008 IEEE Trans. Ultraso. Ferro. Freq. Control 55:2626-2639.*

Irshad et al. Early clinical experience with color 3-dimensional intravascular ultrasound in peripheral interventions. 2001 J. Endovasc. Ther. 8:329-338.*

Ma et al. Control of shape memory alloy actuator using pulse width modulation. 2003 Smart Mater. Struct. 12:712-719.*

International Searching Authority/KIPO, "Notification of Transmittal of the International Search Report and the Written Opinion of the International Searching Authority, or the Declaration," for PCT/US2013/040545, dated Aug. 23, 2013, 10 pages.

* cited by examiner

DEVICE, SYSTEM AND METHOD FOR FLOW IMAGING IN THE BODY USING A SWEPT TRANSDUCER

CROSS-REFERENCE TO RELATED APPLICATION

This application claims priority to and the benefit of U.S. Provisional Application No. 61/646,083, filed May 11, 2012, which is hereby incorporated by reference in its entirety.

BACKGROUND

The development of new imaging technologies has provided an increasing number of options available to doctors for the diagnosis and treatment of disease. For example, intravascular imaging technologies have enabled doctors to create and view a variety of images generated by an imaging device inserted within a vasculature. Often these high quality images are generated in substantially real time. Such images complement traditional radiological imaging techniques (e.g., angiography) by providing images of the tissue and/or blood flow within vessels.

Imaging portions of a patient's body provides a useful tool in various areas of medical practice for determining the best type and course of treatment. For example, imaging of the coronary vessels of a patient by techniques involving intravascular insertion of a catheter-mounted probe (e.g., an ultrasound transducer array) can provide physicians with valuable information. Such image data indicates the extent of a stenosis in a patient, reveals progression of disease, and helps determine whether procedures such as angioplasty or atherectomy are indicated or whether more invasive procedures are warranted.

Ultrasound imaging is widely used in interventional cardiology as a diagnostic tool to establish the need for treatment of a diseased artery, to determine the most appropriate course of treatment, and to assess the effectiveness of the treatment. For example, intravascular ultrasound (IVUS) and intracardiac echocardiography (ICE) catheters are used in the diagnosis and treatment of cardiovascular pathologies including, without limitation, atherosclerosis, heart arrhythmia, heart valve irregularities, and atrial fibrillation. These techniques employ one or more small transducers arranged towards the end of a catheter to provide electronically transduced echo signals to an external imaging system in order to produce a two or three-dimensional image of the lumen, the vessel tissue, and/or the tissue surrounding the vessel. IVUS analysis finds particular application to a system and method for quantitative component identification within a vascular object, including characterization of tissue and identification and analysis of fluid flow.

Traditionally, color Doppler techniques to visualize motion have relied on solid-state phased array catheters with stationary transducers that repeatedly sample a one dimensional space (e.g., a line) in rapid succession to create a "flow group" from which a single line of a two-dimensional F-mode image is extracted from Doppler data. However, IVUS imaging systems utilizing phased array devices are limited in both size and frame-rate, thereby limiting the color flow imaging functionality of phased array catheters in cardiac applications. The size is limited because acceptable grayscale/B-mode imaging requires multiple element transducer systems, and the presence of the multiple elements as well as the wiring and electronics necessary to drive these arrays increase the size of the device far beyond that of a single-element swept transducer system. The frame-rate is limited by the method in which these arrays acquire flow data. In particular, these arrays acquire flow data through the use of flow groups, which are obtained by firing multiple, successive lines from the same element at a high rate. The flow group method reduces the frame rate relative to B-mode imaging by a factor equal to the number of lines in the flow group.

Accordingly, there is a need for devices, systems, and methods that can image flow using a swept transducer to differentiate between dynamic and static contents within a vessel. The devices, systems, and methods disclosed herein overcome one or more of the deficiencies of the prior art.

SUMMARY

Embodiments of the present disclosure describe an ultrasound imaging system including a swept transducer to image flow and other features to render it suitable for differentiating between dynamic and static contents within a vessel.

In one aspect, the present disclosure provides an ultrasound imaging system that includes an ultrasound emitter and receiver movably disposed within an elongate member. An actuator is coupled to the emitter, the actuator moving the emitter through a path comprising at least a portion of an arc. The imaging system also includes a control system controlling the emission of a sequence of pulses from the emitter and receiving from the receiver ultrasound echo data associated with the sequence of pulses emitted along the path, the control system processing the ultrasound echo data to generate an image based on echo amplitude data and echo velocity data.

In another aspect, the disclosure provides an imaging system insertable into an internal structure of a patient. The system comprising an elongate member having a longitudinal axis extending along a distal portion, with the elongate member having an energy emitter and receiver disposed adjacent the distal portion. In one aspect, the receiver is configured to collect echo velocity data and echo amplitude data while an actuator coupled to the energy emitter moves the energy emitter through a path comprising a series of positions along at least a portion of an arc. A control system coupled to the elongate member is configured to control the position of the energy emitter and an energy pulse generated by the energy emitter at each position along the path. The control system receives at least one of the echo velocity data and the echo amplitude data collected by the receiver and processes at least one of the echo velocity data and the echo amplitude data to generate an image of the internal structure.

In another aspect, the present inventions includes a method of imaging an internal structure of a patient. The method comprises positioning an elongate member having a distal portion with a longitudinal axis within the vessel, the elongate member including an emitter and receiver movably mounted within the distal portion. In one aspect, the method includes emitting a sequence of ultrasound beams from the emitter while moving the emitter from a first position to a second position through at least a portion of an arc with respect to the longitudinal axis; and receiving return echoes having echo amplitude data and echo velocity data from structure features including fluid within the structure. The method includes processing the echo amplitude data from the return echoes to generate a composite amplitude ray associated with a position along the arc, and processing the echo velocity data from the return echoes to estimate the velocity of reflecting features at each pixel of the amplitude ray. The method includes generating a display of the structure image reflecting the echo amplitude data and the echo velocity data.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure. Throughout this description, like elements, in whatever embodiment described, refer to common elements wherever referred to and referenced by the same reference number. The characteristics, attributes, functions, interrelations ascribed to a particular element in one location apply to those elements when referred to by the same reference number in another location unless specifically stated otherwise.

The figures referenced below are drawn for ease of explanation of the basic teachings of the present disclosure only; the extensions of the figures with respect to number, position, relationship and dimensions of the parts to form the preferred embodiment will be explained or will be within the skill of the art after the following description has been read and understood. Further, the exact dimensions and dimensional proportions to conform to specific force, weight, strength and similar requirements will likewise be within the skill of the art after the following description has been read and understood.

The following is a brief description of each figure used to describe the present invention, and thus, is being presented for illustrative purposes only and should not be limitative of the scope of the present invention.

Figure 1:
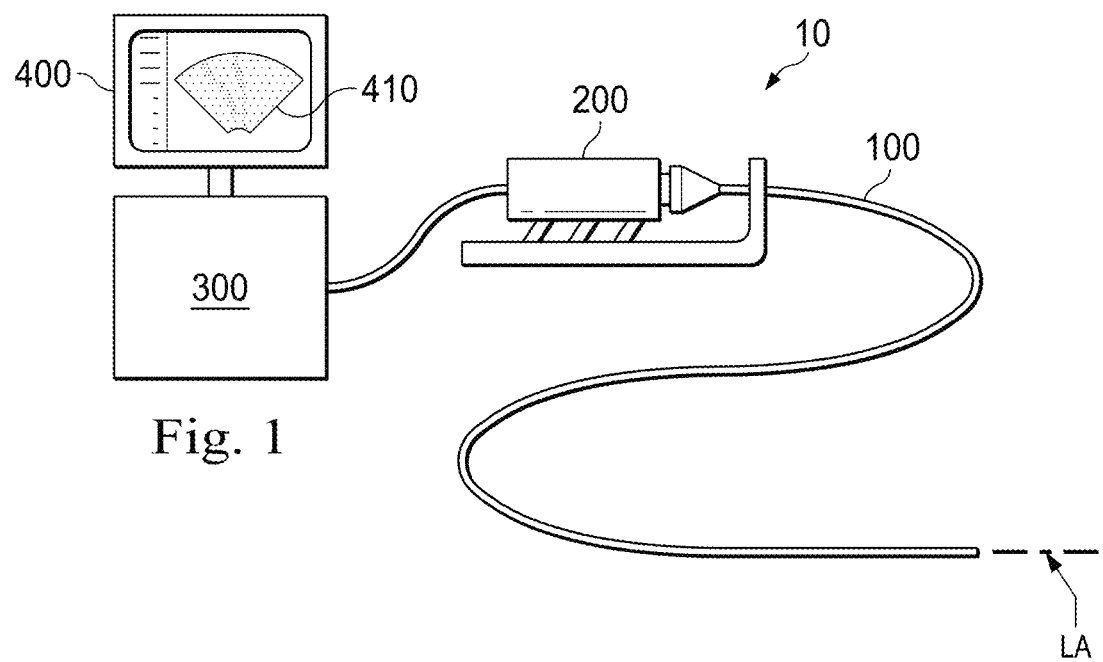

FIG. 1 is a schematic illustration of an exemplary IVUS imaging system, including an exemplary elongated member, according to one embodiment of the present disclosure.

Figure 2:

FIG. 2 is an illustration of a partial cross-sectional side view of an exemplary distal end portion of the elongated member shown in FIG. 1 according to one embodiment of the present disclosure.

Figure 3A:
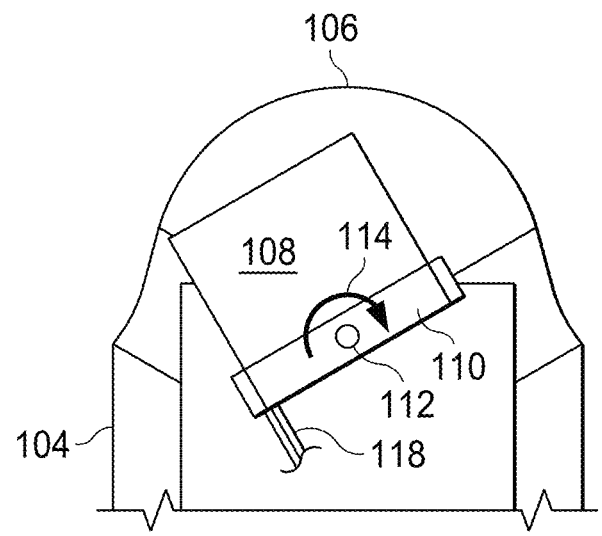

FIG. 3a is an illustration of a partial cross-sectional side view of a distal end portion of the elongated member shown in FIG. 2, illustrating an exemplary transducer element of the imaging system in a first orientation according to one embodiment of the present disclosure.

Figure 3B:
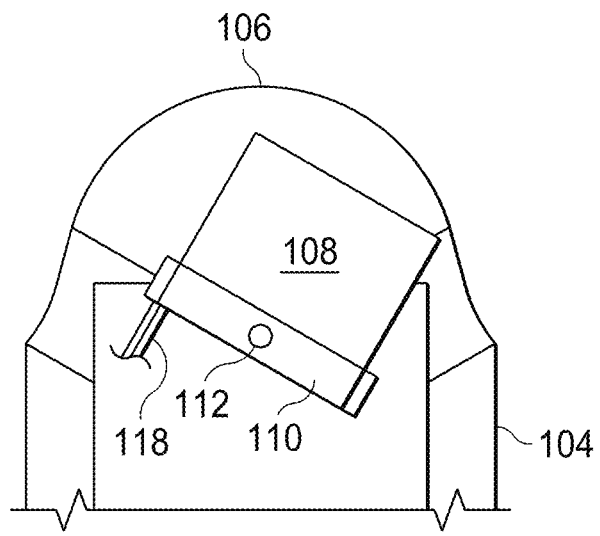

FIG. 3b is an illustration of a partial cross-sectional side view of the distal end portion of the elongated member similar to that of FIG. 3a, but illustrating the transducer element in a second orientation according to one embodiment of the present disclosure.

Figure 4:
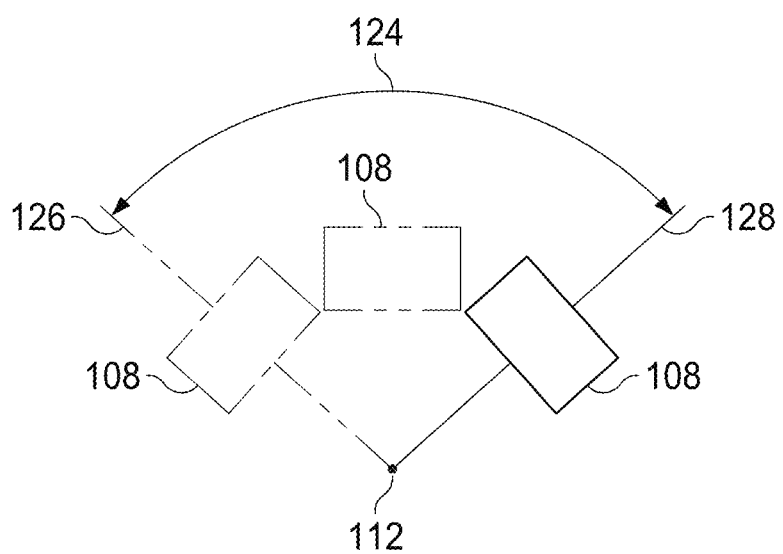

FIG. 4 is a diagrammatic illustration of a schematic view of a motion path of a transducer element of the elongated member of FIG. 2.

Figure 5:
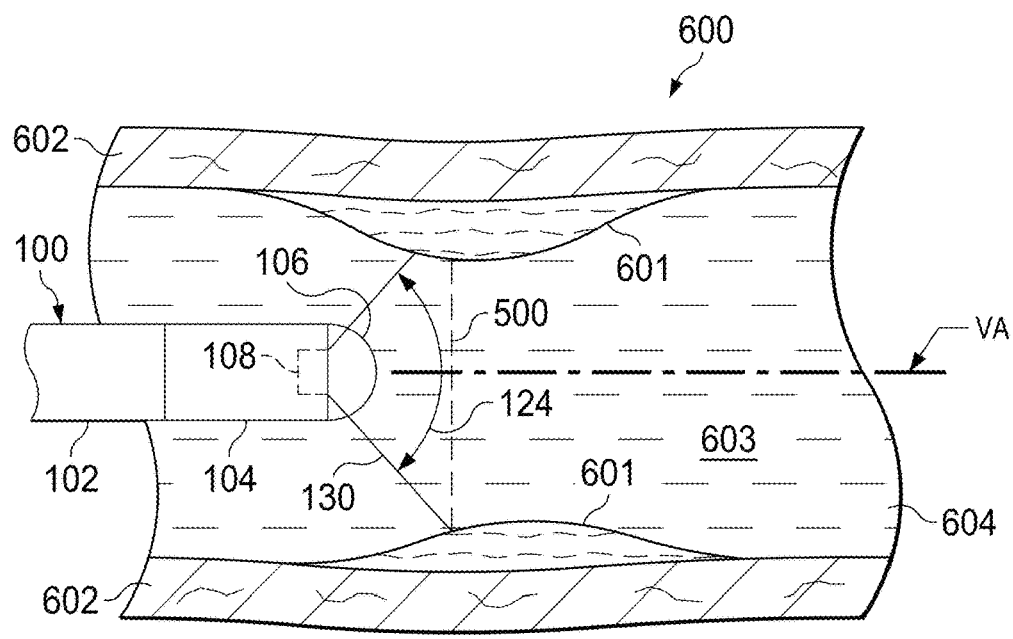

FIG. 5 is an illustration of a partially cross-sectional view of the elongated member shown in FIG. 1 positioned within an artery according to one embodiment of the present disclosure.

Figure 6:
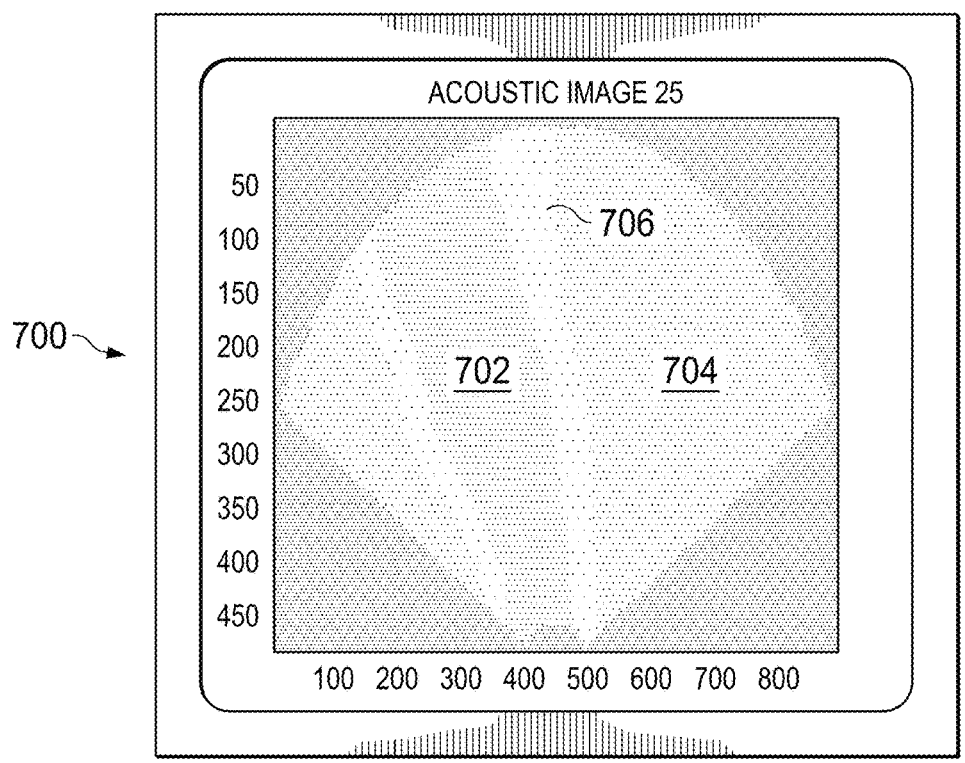

FIG. 6 is an illustration of an IVUS grayscale image according to one embodiment of the present disclosure.

Figure 7:
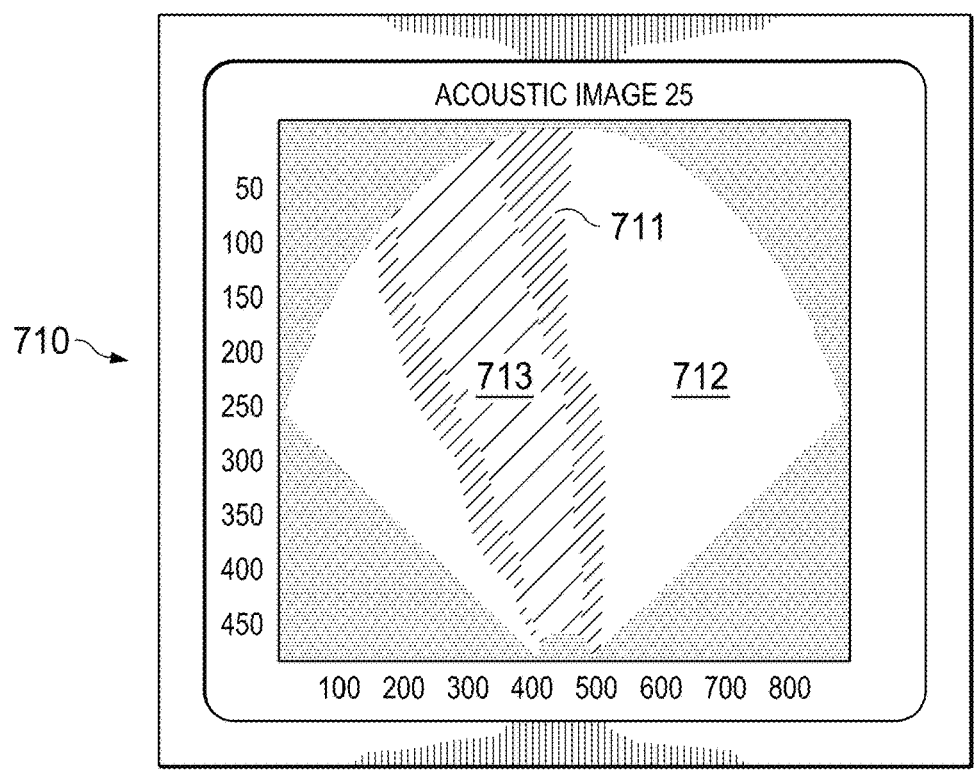

FIG. 7 is an illustration of an IVUS velocity image according to one embodiment of the present disclosure.

Figure 8:
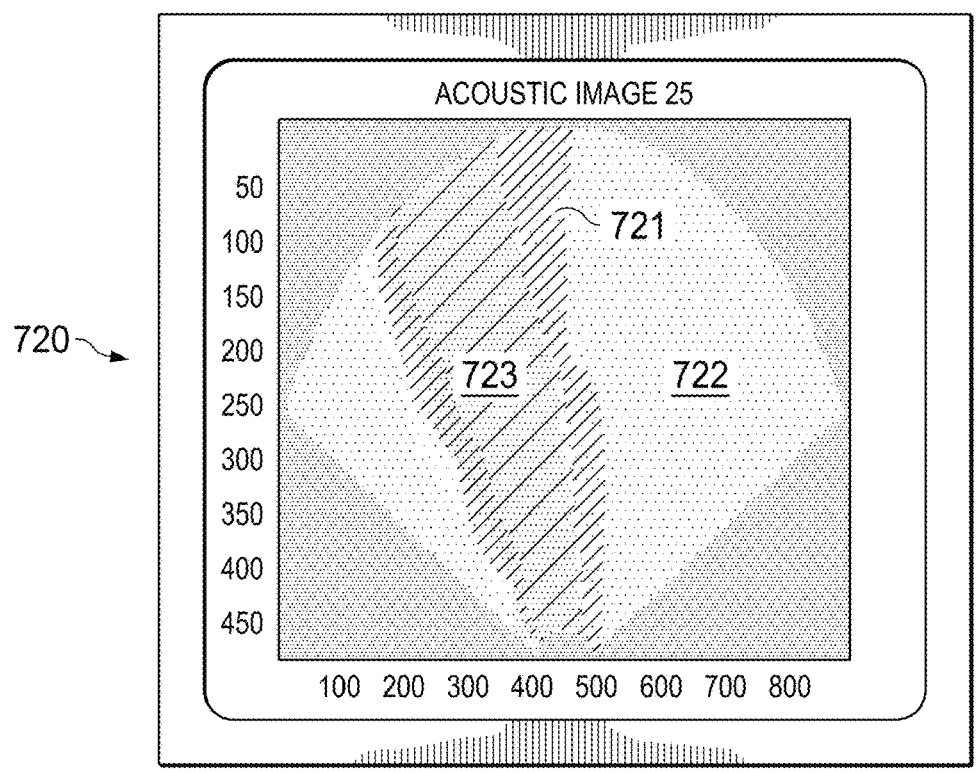

FIG. 8 is an illustration of a hybrid Color Flow IVUS image according to one embodiment of the present disclosure.

Figure 9:
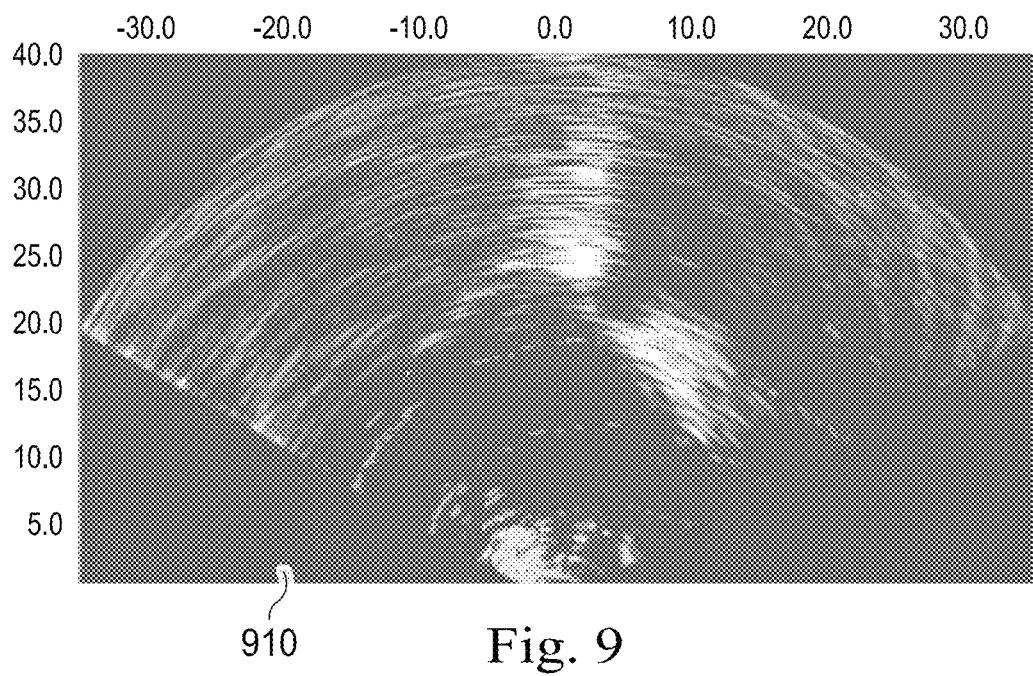
Figure 10:
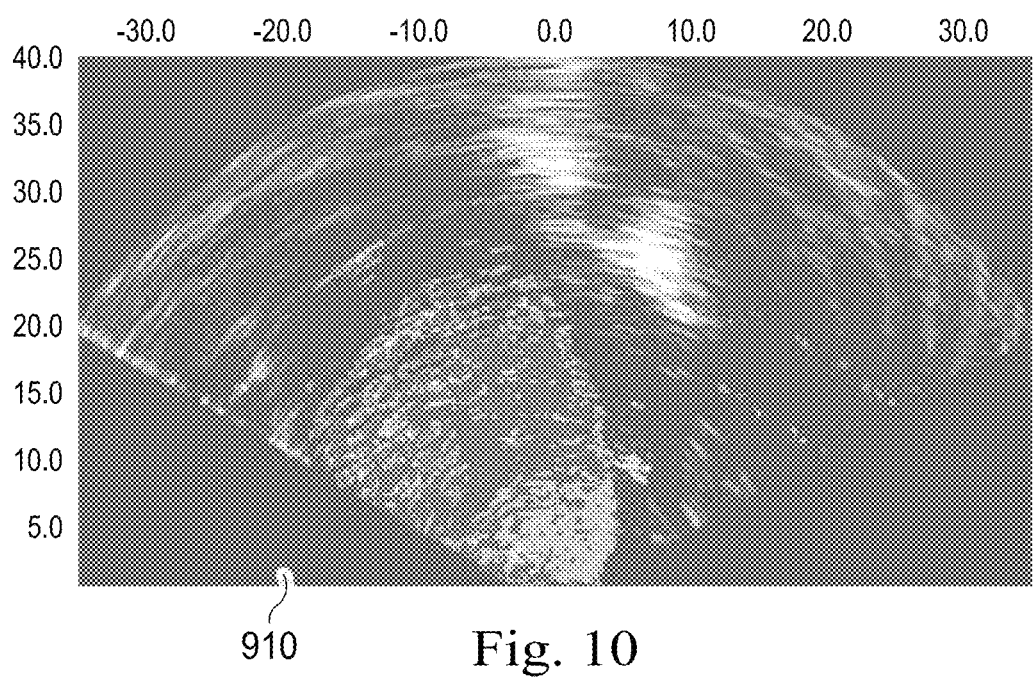
Figure 11:
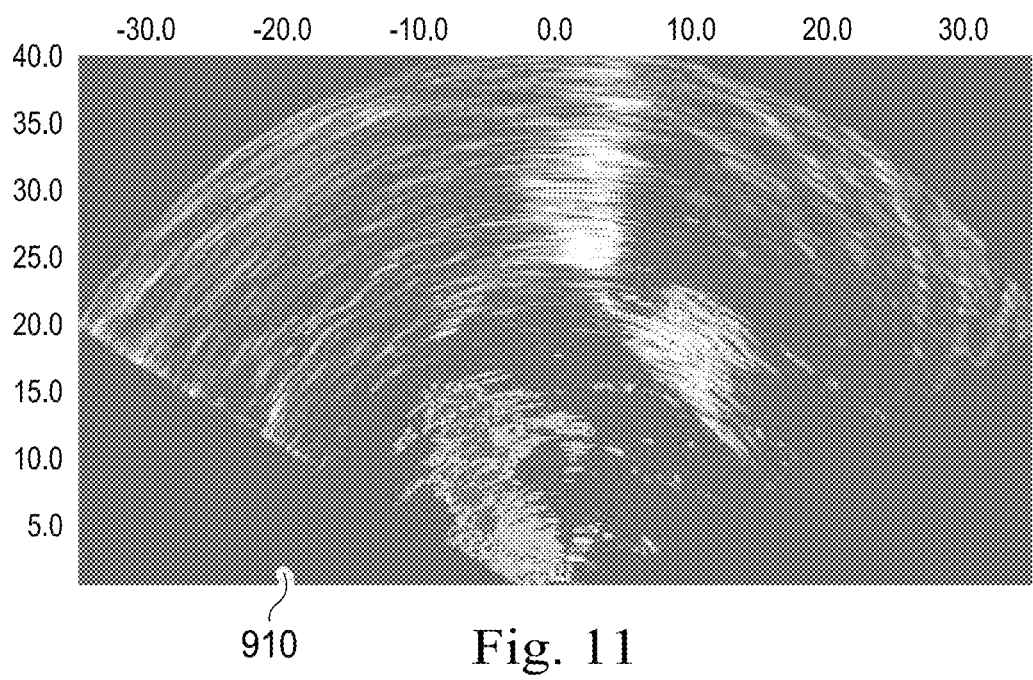

FIGS. 9-11 illustrate exemplary hybrid Doppler color flow images in accordance with the principles of the present disclosure.

Figure 12:
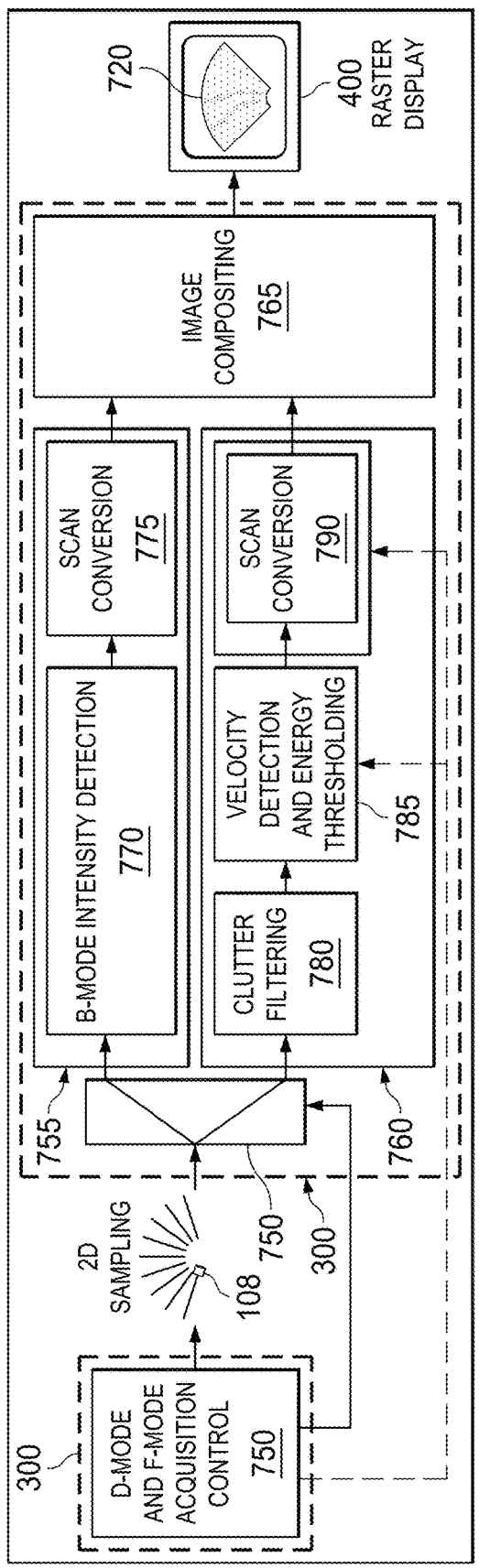

FIG. 12 is a simplified block diagram of individual hardware components of the IVUS imaging system shown in FIG. 1 used to construct a hybrid Color Flow IVUS image according to one embodiment of the present disclosure.

Figure 13:
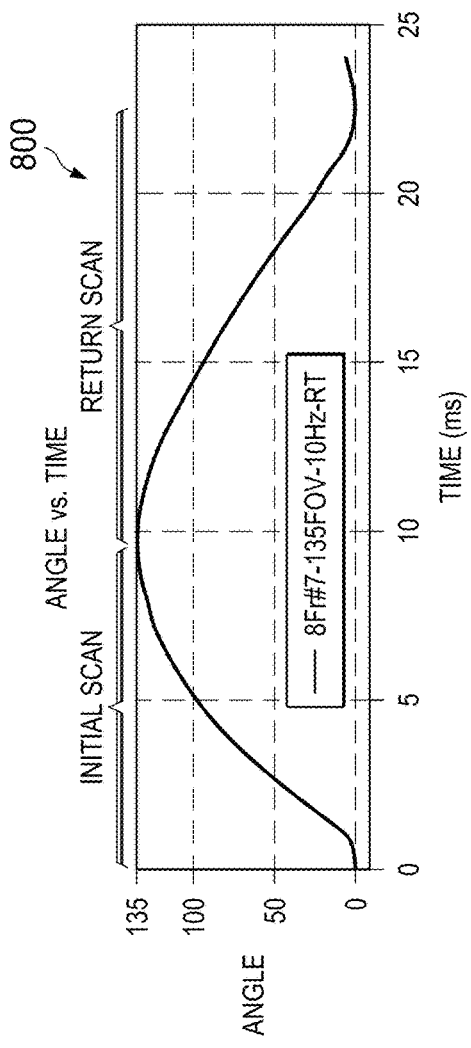

FIG. 13 is a line graph illustrating an exemplary scanning table reflecting the angular spatial sampling provided by a swept transducer used in an imaging system.

Figure 14:
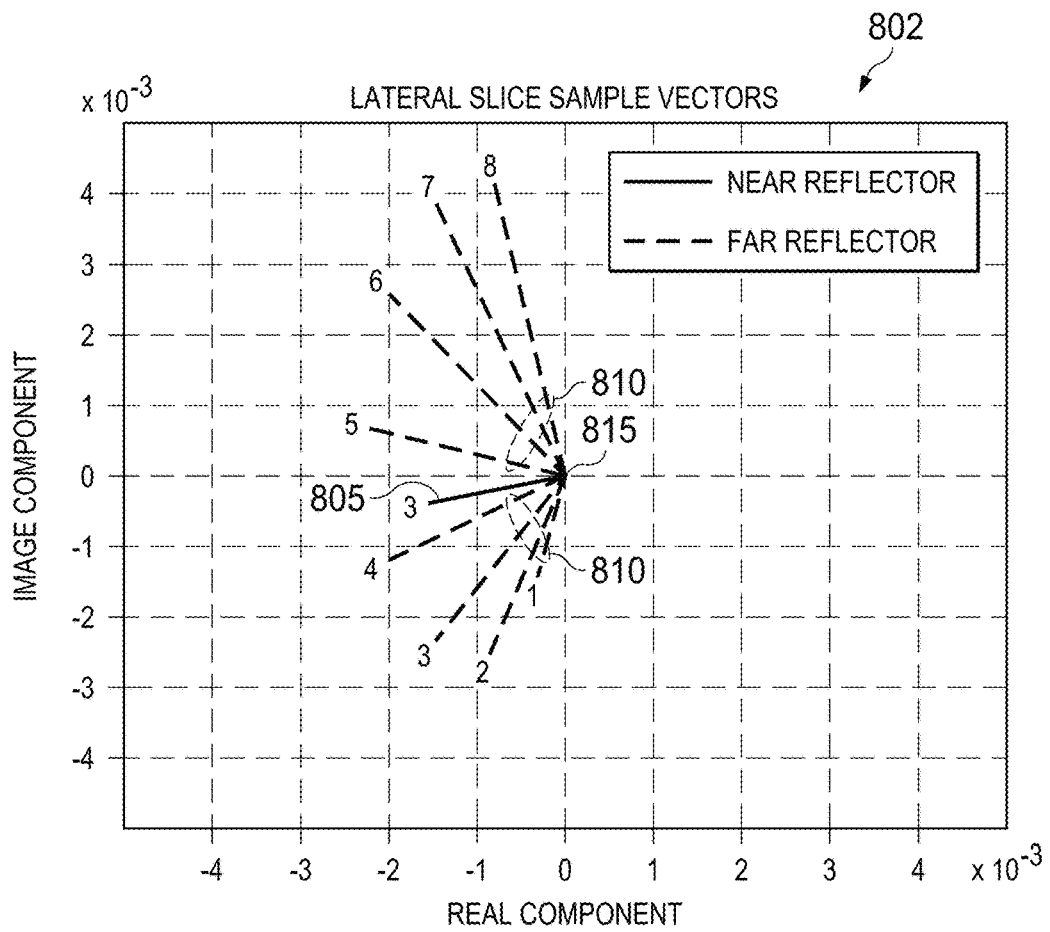

FIG. 14 is a line graph illustrating vectors of an exemplary flow group obtained in accordance with principles of the present disclosure.

Figure 15:
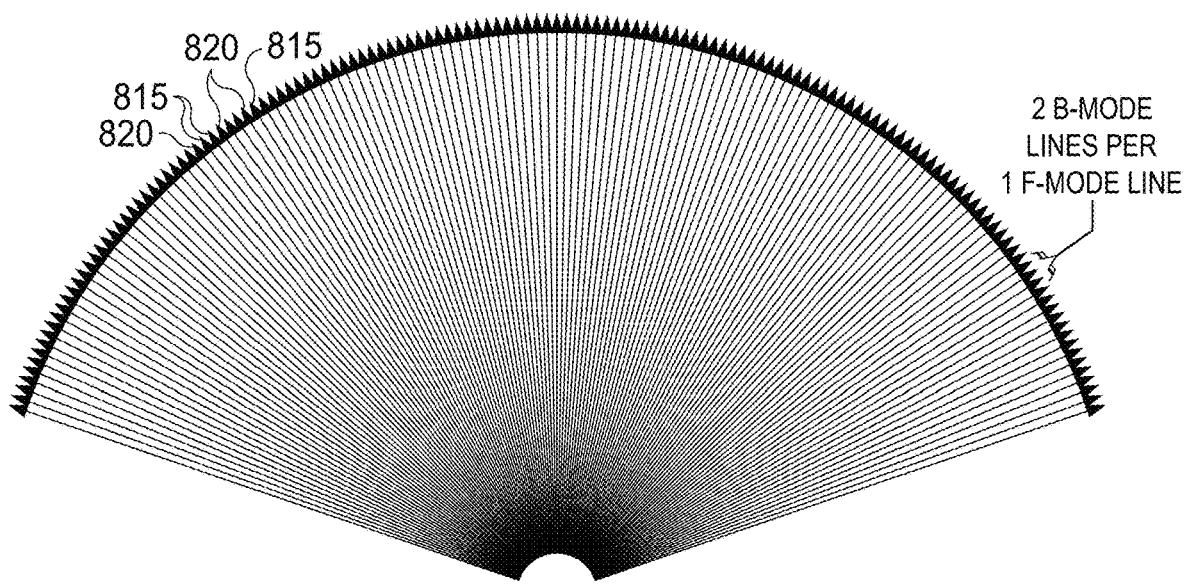

FIG. 15 is a diagrammatic illustration of an exemplary sequence of interleaved ultrasound scan lines of varying imaging modalities obtained in accordance with principles of the present disclosure.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

The present disclosure describes devices, systems, and methods for producing flow images from a movable energy emission device, such as an ultrasound transducer, deployable with an imaging system to facilitate interpretation of cross-sectional images of a patient's internal structures, such as a blood vessel of interest, and to facilitate the qualitative or quantitative measurement of fluid flow through the vessel. In particular, the disclosure describes one embodiment of the devices, systems, and methods that produce an IVUS image with the addition of velocity data encoded as a color map on a grayscale IVUS image to enhance the differentiation between moving blood echoes and stationary tissue echoes.

It should be appreciated that while the exemplary embodiment is described in terms of an ultrasonic device, or more particularly the use of IVUS data (or a transformation thereof) to render images of a vascular object, the present disclosure is not so limited. Thus, for example, using backscattered data (or a transformation thereof) based on ultrasound waves or even electromagnetic radiation (e.g., light waves in non-visible ranges such as used in Optical Coherence Tomography, X-Ray CT, etc.) to render images of any tissue type or composition (not limited to vasculature, but including other structures within a patient including human as well as non-human structures) is within the spirit and scope of the present disclosure.

Referring to FIG. 1, shown therein is an imaging system 10 according to one embodiment of the present disclosure. As shown in FIG. 1, the imaging system 10 includes an elongated member 100 coupled by a patient interface module (PIM) 200 to a control system 300. The control system 300 is coupled to a color monitor 400 that can display a flow image 410. In some instances, the flow image 410 is a color image.

In the pictured embodiment, the imaging system 10 includes the components associated with a typical IVUS module, such as transducer(s), multiplexer(s), electrical connection(s), etc., for performing IVUS imaging. It is understood that, in some instances, wires associated with the imaging system 10 extend from the control system 300 to the PIM 200 such that signals from the control system 300 can be communicated to the PIM 200 and/or visa-versa. In some instances, the control system 300 communicates wirelessly with the PIM 200. Similarly, it is understood that, in some instances, wires associated with the IVUS imaging system 10 extend from the control system 300 to the color monitor 400 such that signals from the control system 300 can be communicated to the color monitor 400 and/or visa-versa. In some instances, the control system 300 communicates wirelessly with the color monitor 400.

The elongated member 100 is shaped and configured for insertion into a lumen of a blood vessel (not shown) such that a longitudinal axis LA of the catheter 100 aligns with a longitudinal axis of the vessel at any given position within the vessel lumen. In that regard, the curved configuration illustrated in FIG. 1 is for exemplary purposes only and in no way limits the manner in which the catheter 100 may curve in other embodiments. Generally, the elongate member 100 may be configured to take on any desired arcuate profile when in the curved configuration.

Referring to FIGS. 2-3b, shown therein are aspects of the elongated member 100 according to an embodiment of the present disclosure. More specifically, FIG. 2 is a diagrammatic schematic view of a portion of the elongated member 100; FIG. 3a is a partial cross-sectional side view of a distal end portion of the elongated member 100, illustrating a transducer element of the imaging system in a first orientation; and FIG. 3b is a partial cross-sectional side view of the distal end portion of the elongated member 100, similar to that of FIG. 3a, but illustrating the transducer element in a second orientation.

In general, the elongated member 100 is sized and shaped for use within an internal structure of a patient, including but not limited to a patient's arteries, veins, heart chambers, neurovascular structures, gastrointestinal system, pulmonary system, and/or other areas where internal imaging of patient anatomy is desirable. In that regard, depending on the particular medical application, the elongate member 100 is configured for use in cardiology procedures, neurovascular procedures, pulmonary procedures, endoscopy procedures, colonoscopy procedures, natural orifice procedures (such as Natural Orifice Transluminal Endoscopic Surgery (NOTES)), and/or other medical procedures. Accordingly, in some embodiments the elongate member 100 takes the form of a guidewire or catheter.

It should be noted that the elongated member 100 depicted herein is not limited to a particular type of device, and includes any of a variety of imaging devices. For example, a catheter or a guidewire having a single transducer adapted for rotation and/or forward-looking is contemplated as within the spirit and scope of the present disclosure. As an example in that regard, in some instances, the catheter 100 includes components or features similar or identical to those disclosed in U.S. Provisional Patent Application No. 61/646,080, entitled "Device and System for Imaging and Blood Flow Velocity Measurement," filed May 11, 2012, which is hereby incorporated by reference in its entirety.

In the embodiment shown in FIG. 2, the elongated member 100 is a forward-looking IVUS catheter. The elongated member or catheter 100 includes a flexible body 102 having a distal housing portion 104 extending to a distal tip 106. In the pictured embodiment, the distal housing portion 104 houses a transducer 108. One or more radiopaque markers 105 may be incorporated into the elongate member.

As shown in FIG. 3a, a transducer 108 is disposed within the distal housing portion 104 adjacent the distal tip 106. In some instances, the transducer 108 is an ultrasound transducer that is configured to transmit ultrasound signals and receive backscatter data. In the illustrated embodiment, the transducer 108 is mounted on a platform 110 that is configured to rotate at least partially about an axis defined by a pivot pin 112 extending through a portion of the platform 110. In that regard, transducer 108 rotates—in the direction of arrow 114—from an initial orientation (shown in FIG. 3a) to a fully-rotated orientation (shown in FIG. 3b). From the fully-rotated orientation, the transducer rotates—in the direction opposite of arrow 114—back to the initial orientation. This process is repeated to cause oscillation of the transducer 108 about pivot pin 112.

In the illustrated embodiment, the platform 110 interfaces with an actuator 118 to facilitate oscillation of the transducer 108. FIG. 3a shows the transducer 108 in an initial position. The actuator 118 causes the platform 110 to rotate about the pivot pin 112 in the direction of the arrow 114, which moves the platform 110 to a second position, as shown in FIG. 3b. Rotation of the platform 110 sweeps the transducer 108 from the initial position (FIG. 3a) to the fully-rotated position (FIG. 3b), and vice versa. In some embodiments, the transducer 108 comprises an actuator-driven swept transducer, as shown in FIGS. 3a and 3b. In other embodiments, the transducer 108 comprises a motor-driven swept transducer. In that regard, the actuator 118 may comprise any of a variety of movement-inducing mechanisms, including, by way of non-limiting example, a motor, a magnet, or an actuator formed of shape memory material.

While FIGS. 3a and 3b illustrate the transducer 108 being oscillated, in other instances the transducer 108 is maintained in a fixed position and a minor or other reflective element is oscillated. In that regard, the mirror or other reflective element reflects the signals generated by the fixed transducer (e.g., acoustic waves associated with ultrasound imaging) such that the signals are swept through the motion profile in a manner similar to when the transducer itself is oscillated.

FIG. 4 illustrates an exemplary motion profile of the transducer 108. As shown, the transducer 108 pivots about the pivot pin 112 and travels across an angle or angular range 124 between a starting orientation (represented by axis 126 and the transducer 108 shown in phantom on the far left of the drawing) and an ending orientation (represented by axis 128 and the transducer 108 shown on the far right of the drawing). In that regard, the angle 124 between the starting orientation and the ending orientation that the transducer 108 travels is generally between about 1 degree and about 400 degrees, depending on the imaging application. In some instances, the angle 124 is between about 25 degrees and about 360 degrees. Still further, in one application the imaging arc or angular range 124 of the transducer is between 90 degrees and 270 degrees. It is understood, however, that the present disclosure is applicable to any amount of transducer rotation and no limitation is intended by these exemplary ranges.

In some instances, a user may maneuver the catheter 100 through a patient's body to an area of interest. The user may then control the movement of the transducer 108 via the control system 300 and/or the PIM 200 to emit ultrasound pulses and receive backscattered signals from vascular tissue, plaque, and/or blood. For example, FIG. 5 illustrates a distal portion of the body 102, including the distal housing 104, of the catheter 100 positioned within a vessel 600, which includes a lesion 601 positioned against a vessel wall 602 and within a lumen 603. In FIG. 5, the catheter 100 is shown positioned within moving blood 604 of the lumen 603 of the vessel 600 such that the axis LA of the catheter 100 (shown in FIG. 1) is substantially parallel to a longitudinal axis VA of the vessel 600 (and of the blood flow).

In the embodiment shown in FIG. 5, the transducer 108 comprises a single-element transducer that is swept back and forth or rotated to cover a sector over the selected angular range 124. As the transducer 108 is swept through the sector, many acoustic lines (emanating from the transducer) are processed to build up a sector-shaped cross-sectional image of tissue within the patient. An ultrasound beam 130 emerges from the transducer 108 and, as the transducer 108 oscillates, sweeps out an imaging surface 500 to produce an ultrasound image 700 of the vessel 600. In other embodiments, the transducer may be tilted within the distal housing 104 and/or the actuator may rotate the transducer.

As the transducer 108 oscillates inside the distal housing 104, the transducer 108 sends the ultrasound beam 130 toward the vessel wall 602. Reflections from the ultrasound beam 130 as it contacts reflectors within the vessel 600, including the lesion 601, the vessel wall 602, and the moving blood 603, are received by the transducer 108. These ultrasound echoes are transmitted to the control system 300 via the PIM 200 (shown in FIG. 1), and the imaging system 10 processes the echoes to create a tomographic grayscale image of the vessel.

With reference back to FIG. 1, during operation of the imaging system 10, the control system 300 cooperates with the PIM 200 to generate an appropriate sequence of ultrasound transmit/receive cycles at each image angle to permit the extraction of velocity information from the echo signals. During a brief time period following each transmitted pulse from the transducer 108, the echo signals from the surrounding tissue and blood are received by the transducer 108 and detected by the control system 300. Because different types and densities of tissue absorb and reflect the ultrasound pulses differently, the control system 300 utilizes the reflected backscatter data (i.e., the IVUS data) transmitted back to the control system 300 to assemble a two-dimensional ultrasound image of a blood vessel from hundreds of pulse/acquisition cycles.

In some embodiments, the control system 300 includes signal processing hardware to simultaneously extract velocity estimates to provide color encoding of the moving blood along with the traditional echo strength data for the grayscale IVUS display. The color monitor 400 displays the hybrid color flow image 410 comprised of the grayscale IVUS image with the moving blood echoes highlighted in color to convey information regarding the magnitude and direction of blood velocity. In some instances, the grayscale IVUS image and/or the hybrid color flow image may be co-registered with other imaging data such as angiogram, MRI, and fluoroscopy. More specifically, radiopaque markers 105 on the elongate member 100 may be imaged with one or more imaging systems and the output image of system 10 displayed in a co-registered manner with the image information of the additional imaging system.

FIG. 6 shows a schematic illustration of an exemplary grayscale image 700 of the vessel 600. In the grayscale image 700 depicted in FIG. 5, the distinction between blood echoes 702 and vessel wall echoes 704 is not great. Particularly at the higher ultrasound frequencies preferred for high resolution IVUS imaging, the distinction between blood echoes and vessel wall or plaque echoes is subtle. The strength of an ultrasound echo is strongly influenced by the size of the reflecting object compared to the ultrasound wavelength. For example, at a 20 MHz ultrasound frequency, the echo from the vessel wall tissue is typically much stronger than the echo from the moving blood, since the blood cells are much smaller (approximately 6 µm in diameter) than the coherent tissue structures that make up the vessel wall (e.g., collagen fibers, smooth muscle cells, tissue layers, etc.) and much smaller than the ultrasound wavelength (approximately 75 µm). In contrast, at a 40 MHz ultrasound frequency, the contrast between vessel wall echoes 704 or plaque tissue echoes 706 and blood echoes 702 is diminished because the shorter acoustic wavelength (approximately 40 µm) more closely approaches the diameter of the blood cells. The low image contrast between the blood and the vessel wall tissue may make it difficult to identify the boundaries of the lumen and to quantify anatomic parameters such as diameter or cross-sectional area of the vessel 600, which are helpful to guiding the treatment of the coronary artery disease.

It is important to note that noninvasive color flow imaging systems cannot take advantage of high ultrasound frequencies, such as 40 MHz, due to the frequency-dependent attenuation of the ultrasound in tissue which severely limits the penetration depth. Noninvasive color flow imaging systems cannot take advantage of such high ultrasound frequencies because the high ultrasound frequency results in large Doppler frequency shifts that necessitate a high pulse repetition frequency and short period between successive ultrasound pulses, thereby limiting the usable penetration depth. However, for IVUS imaging, the shallow penetration depth permits the use of a high pulse repetition frequency adequate to capture the maximum velocity likely to be encountered in a physiological environment. For IVUS imaging, the required penetration depth is shallow enough that the attenuation in blood, even at a 40 MHz ultrasound frequency, is low enough to allow adequate signal to noise ratio.

To improve the diagnostic value of the grayscale IVUS image 700, as described later with respect to FIG. 12, the control system 300 utilizes a separate signal processing path that may operate in parallel or in series with the standard imaging path to provide information about the relative velocities of components within the vessel 600. While the standard image processing algorithm translates the amplitude of the echo signal into grayscale brightness on the display image 700, the parallel signal processing path extracts a velocity estimate for every pixel of the display image 700. In some embodiments, the parallel signal processing path extracts the velocity estimates from the information contained in the Doppler frequency shift of the return echo signals.

FIG. 7 illustrates the image that would be obtained if the imaging system 100 was programmed to display an image 710 of the velocities of the ultrasound echoes received by the transducer 108 instead of the amplitudes of the ultrasound echoes received by the transducer 108. A lesion representation 711 and a vessel wall representation 712 of the velocity image 710 would indicate low velocities for the relatively static lesion 601 and vessel wall tissue 602, respectively, while the relatively fast-moving blood 604 within the vessel lumen 603 would be prominently highlighted by the blood representation 713. For example, but not by way of limitation, the echo velocities may by displayed in the velocity image 710 in shades of red and blue for antegrade and retrograde flow, respectively, while relatively stationary or slow-moving tissues may be displayed in shades of black and white or grey. In one embodiment, the lesion representation 711 and the vessel wall representation 712 may appear in shades of grey to reflect the relatively static or slow-moving lesion 601 and vessel wall 602, while the blood representation 713 is highlighted in color. In the pictured embodiment, the lesion representation 711 may appear with some areas of color to reflect blood moving over the luminal contours of the lesion.

In practice, the separate grayscale IVUS image 700 and velocity image 710 may be difficult to interpret, and a synergistic image may be achieved by combining the echo amplitude data and echo velocity data together in a hybrid flow image 720, as shown in FIG. 8, in which the echo amplitude is encoded as image brightness and echo velocity is encoded in color. In the hybrid color flow image 720, the stationary lesion 721 and vessel wall 722 appear in black and white and shades of grey much the same as in a conventional IVUS image, while the representation 723 of moving blood is highlighted in color by virtue of its velocity-related Doppler frequency shift. The enhanced image contrast between the blood 723 and the vessel wall 722 in the color flow image 720 makes it much easier (compared to traditional IVUS imaging) for the user and/or the system 300 to identify the boundary of the vessel lumen 603 and to quantify anatomic parameters such as diameter or cross-sectional area of the vessel 600, which are important for guiding the treatment of cardiovascular disease. In other embodiments, the echo velocity data may be encoded on the hybrid flow image in a manner other than color, including by way of non-limiting example, textures or patterns.

FIGS. 9-11 illustrate exemplary hybrid Doppler color flow images in accordance with the principles of the present disclosure. In particular, FIGS. 9-11 illustrate hybrid Doppler color flow images obtained by a swept, single-element, forward-looking ultrasound catheter placed inside a vessel adjacent an aortic valve of an animal. Areas 910 represent colorized portions of the images indicating blood flow.

FIG. 12 presents a simplified block diagram illustrating individual hardware components of the imaging system 10 used to construct a color flow IVUS image according to one embodiment of the present disclosure. As described above in reference to FIG. 1, the imaging system 10 according to an exemplary embodiment, includes the transducer 108 of the catheter 100, the color monitor 400, and the IVUS control system 300, which coordinates and controls the operation of the IVUS imaging system. In the pictured embodiment, the control system 300 comprises a host of computing modules, including, but not by way of limitation, an acquisition controller 750, a B-mode (i.e., intensity-related) module 755, an F-mode (i.e., flow-related) module 760, and an image compositor 765. In the pictured embodiment, the B-mode module 755 includes a grayscale analyzer 770 and a B-mode scan converter 775. In the pictured embodiment, the F-mode module includes a clutter filter 780, a velocity computer 785, and an F-mode scan converter 790. The embodiment detailed in FIG. 12 is well-suited to implementation in a field programmable gate array (FPGA), which can incorporate the entire digital signal processing chain for the IVUS imaging system 10 in a single integrated circuit device.

The acquisition controller 750 is capable of collecting B-mode and F-mode data simultaneously or in a variety of interleaved fashions with temporal and spatial resolution tradeoffs made appropriately for each particular application. Spatial sampling is performed by the transducer 108, which sweeps continuously at low angular velocities that may vary in time. This variable angular velocity profile may be known a priori or measured using a rotational encoder.

FIG. 13 shows an exemplary scanning table 800 according to one embodiment of the present disclosure. The angular, or lateral, spatial sampling provided by the swept transducer 108 may follow a non-linear angle versus time curve, as displayed in FIG. 13, which illustrates an example of such a curve for a catheter with a transducer which sweeps from an original position to one angular extent and then returns to the original position. In addition to angular position, the angular velocity of the transducer 108 is known for each F-mode line acquired. As indicated by the graph 800, the duration of the initial scan may be shorter than the duration of the return scan. The imaging system 10 uses the non-linear angular position of the transducer 108 during acquisition when mapping between coordinate systems.

Returning to FIG. 12, the B-mode module 755 and the F-mode module 760 cooperate to construct a hybrid flow image for display on the color monitor 400. In the pictured embodiment, the B-mode module 755 and the F-mode module 760 cooperate to construct a hybrid Doppler Color Flow image. Within the B-mode module 755, the grayscale analyzer 770 and the scan converter 775 function to produce a grayscale image in accordance with techniques known to those of skill in the art. The grayscale analyzer 770 removes the carrier frequency from each echo signal to extract the echo amplitude data or amplitude function, which is translated into gray levels to provide a single ray or radial line (commonly referred to as an A-line) of the grayscale portion of the hybrid color flow IVUS image 720.

Either in series or parallel fashion, as described in more detail below, the grayscale analyzer 770 and the velocity computer 785 process the acquired data to (1) detect the echo amplitude data as a function of depth to generate an A-line, and (2) to calculate the echo velocity data for each position along that ray, respectively. In some instances, the velocity computer calculates the Doppler-derived velocity data for each position along the ray. In other embodiments, the velocity computer uses other velocity-calculating algorithms to derive the echo velocity data. The grayscale analyzer 770 includes amplitude detection circuitry to derive the grayscale image information, while the velocity computer 785 includes phase detection circuitry used to derive the velocity information for color coding the hybrid flow image 720. In the pictured embodiment, the gray scale analyzer 770 uses the information contained in the sequence of echo signals to detect the echo amplitude as a function of depth to generate a single A-line of the grayscale image with a low noise level and wide dynamic range, while the velocity computer 785 calculates the Doppler-derived velocity estimate for each position along that A-line from the small phase changes from one echo signal to the next within a single sequence. The input to both the grayscale analyzer 770 and velocity computer 785 may be used to produce a single hybrid A-Line of the image for each echo signal.

The system 10 displayed in FIG. 1 constructs the flow image 720 by creating flow groups from A-lines obtained from the swept transducer 108. Although the lines with the flow group are not obtained from a stationary element, it is possible to create these flow groups because the sweep velocity of the transducer 108 is low enough to create successive lines that, while not identical in space, are spaced closely together, thereby allowing methods of obtaining blood flow information to be applied to facilitate color flow imaging. One such method of obtaining blood flow information is the phase shift estimation method using autocorrelation. Generally, a time shift in the received pulse due to a moving reflector at a given depth results in a phase shift between equivalent depth samples in consecutive lines, and this phase shift can then be mapped to the reflector velocity. The received ultrasound data is demodulated and a matched filter is convolved with the data in the axial dimension resulting in a series of complex values. The matched filter output is a weighted range gate.

FIG. 14 is a range gate illustration of a line graph 802 showing vectors for a flow group of eight for a moving target and a stationary target. When the axially processed output data is sliced in the lateral dimension, a series of complex values are obtained with vectors plotted as shown in FIG. 14. The vector 805 for the stationary reflector does not vary in phase, while the vectors 810 for the moving reflector are rotating about an origin 815 at a rate proportional to the velocity of the reflector.

Within the F-mode module 760, as in conventional F-mode processing, the clutter filter 780 is used to remove low velocity data, including stationary data, generally from tissue, lesions or non-natural materials. The clutter filter 780 is a lateral high-pass filter used to attenuate the non-rotating, or stationary, vectors. This is helpful because the high intensities of low velocity tissue reflectors make it more difficult to extract phase values for relatively weak reflectors, such as moving blood. The continuous nature of the acquired F-mode information lends itself to different filter topologies, including without limitation, infinite impulse response (IIR) filters. Doppler signals returned from moving blood are typically about 30 dB lower in power from echoes returned by low velocity reflectors, such as, for example, areas of plaque or vessel wall. For that reason, the high-pass clutter filter 780 is used to remove the low velocity echoes prior to velocity estimation by the velocity computer 785. For low flow velocity detection, the clutter filter 780 needs a sharp cutoff at as low a frequency as possible. In conventional F-mode clutter filtering, a finite impulse response filter can be used with a number of taps that is less than the flow group size. This means that the filter transient response is present for each flow group and that the requirements for the clutter filter compete with requirements for frame rate. In the swept single element imaging system 10, the F-mode data acquisition by the acquisition controller 750 is continuous and therefore no fundamental limitation on filter length exists. In the imaging system 10, the clutter filter 780 is a sliding window clutter filter, and thus the transient response affects only the start and end of the frame. This condition opens the possibility of using infinite impulse response filters that can provide a sharper cutoff using fewer samples, but whose transient response is too long for use in the conventional flow group technique. In other embodiments, the clutter filter may be a different type of filter that allows for low flow velocity detection.

The velocity computer 785 of the F-mode module 760 computes clutter-filtered energy and estimates velocity using phase shift or time shift methods across a sliding window of lateral samples. The energy estimate is compared against a controllable threshold and velocity estimates are discarded if energy is insufficient. In conventional F-mode velocity estimation, a single velocity is computed for each overlapping flow group. Average clutter filtered energy across the flow group is also calculated and used as a metric for evaluating the quality of the velocity estimation. However, both the velocity estimate and the energy computation are improved by increasing the flow group size at the expense of frame rate. Velocity estimates can be improved with larger flow groups up to a certain limit; because the lines are not from a stationary element, the larger the flow groups, the less correlated the last sample is with the first sample and the less accurate the flow measurement. In some embodiments of the swept single element imaging system, the F-mode acquisition is continuous and a sliding energy and velocity estimator window is used. The length of this window is independent of the filter length. Frame rate is unaffected by window length or size of the flow group (unlike phased array embodiments), however, flow accuracy may be affected.

In some embodiments, the velocity computer includes phase detection circuitry. Phase detection circuitry used for estimating the Doppler velocity can be implemented using a variety of algorithms known to those skilled in the art. A variety of methods are known to those skilled in the art for extracting a Doppler-derived velocity estimate from a sequence of echo signals. These methods have been applied extensively to noninvasive Doppler color flow ultrasound imaging systems, but heretofore this technology had not been thought to be applicable to swept single-element IVUS imaging systems for the reasons discussed above. The phase detection circuitry is designed to extract a Doppler velocity estimate for each radial position along an A-line of the image, from the sequence of echo signal acquisitions that is obtained from that angular position. The movement of blood or tissue at a particular depth along a ray of the image is encoded in the sequence of echo signals as a rate of change in phase of the echo signal at that radial position. The phase detection circuitry is designed to determine the phase change at every sample depth for each echo signal acquisition, to calculate the change in phase from one echo signal to the next within a sequence, to accumulate the change in phase over the series of echo signal acquisitions within the sequence, and to estimate the tissue or blood flow velocity from the rate of change in phase according to the Doppler equation.

As mentioned above, the Doppler velocity is estimated for each radial position along an A-line by measuring the rate of change of phase at that point. After a complete acquisition sequence is processed, the output of the velocity computer 785 is a single line of velocity data corresponding to the single A-line of grayscale amplitude data provided by the grayscale analyzer 770. As subsequent acquisition sequences are processed, additional lines of grayscale and velocity data are produced and these lines of data are used by the image compositer 765 to paint a complete tomographic image of the vessel, including color encoded velocity information to aid in the interpretation of the image.

In an exemplary method of estimating Doppler velocity, an auto-correlator may be used to estimate the average phase difference between vectors. The first lag output represents the average product of neighboring vectors, the angle of which is the average phase difference. The zero-eth lag is also computed to give the best estimate of the energy present.

The energy estimate is compared against a variable threshold and velocity estimates are discarded if insufficient energy exists. The threshold may be variable on a per-line basis that compensates for the increasing or decreasing quality of velocity estimates due to changing angular velocity. The threshold may also be variable in range to compensate for the increasing or decreasing quality of velocity estimates due to increasing spatial differential due to the angular sampling. The computed phase values at each depth are threshold based on the corresponding computed energy estimate versus the pre-determined threshold. Any sample that has insufficient energy is assigned a phase value of zero. This eliminates the wild phase fluctuation resulting from vectors with very small magnitudes (or the undefined phase of a vector with magnitude equal to zero).

The average phase difference ($\theta$) can be converted to an average angular velocity ($\omega$) value based on the constant pulse repetition interval (PRI) in accordance with the equation, $\omega=\theta/PRI$.

The reflector velocity (v) can be calculated from the average angular velocity ($\omega$), the round-trip speed of sound ($c_o$), the imaging frequency ($f_c$), and the angle between the ultrasound beam and the direction of motion of the target ($\Phi$, the Doppler angle) as follows: $v=[(c_o*\omega)/(2\pi f_c)] \cos \Phi$.

The phase-shift estimation is subject to aliasing. The maximum phase shift that can be measured is dependent on the center frequency and the PRI. The maximum velocity that can be measured is thus determined by the equation, $v_{max}=c_o/(4*PRI*f_c*\cos \Phi)$.

Beyond this maximum velocity, the average phase wraps, turning to the opposite polarity, and incoming flow can be mistaken as outgoing flow and visa-versa. In the swept single-element system 10, the PRI is dependent on the depth of penetration. As such, so is the maximum detectable velocity $v_{max}$. Some tradeoffs can be made by limiting the depth of penetration during F-Mode acquisition.

An additional tradeoff related to PRI (and the depth of penetration), is the spatial sampling and/or collection of flow groups by the swept single-element system 10. As the depth increases, adjacent lines within a flow group become further apart in space and the correlation between lines in an individual flow group decreases.

In some embodiments, the B-mode module 775 and the F-mode module 760 cooperate to build the hybrid color flow image 720 by a method of frame interleaving. Frame interleaving consists of alternating use of the B-mode module 775 and the F-mode module 760 on a per frame basis, i.e., the imaging system 10 performs B-mode and F-mode imaging on alternate frames. This method of frame interleaving may provide the best spatial image quality for both for B-Mode and F-Mode processing. In some embodiments, this is achieved by maximizing the frame line density. Additionally, if ultrasound pulses are optimized for the desired mode in each frame, additional gains such as axial resolution can be achieved. However, the method may reduce the effective frame rate by a factor of 2.

In some other embodiments, the imaging system 10 may collect B-mode and F-mode information to facilitate color flow imaging without sacrificing the frame rate. In some embodiments, the imaging system 10 includes components substantially similar to the imaging systems described in U.S. application Ser. No. 12/992,814 entitled Miniature Forward-Looking Ultrasound Imaging Mechanism Enabled by Local Shape Memory Alloy Actuator and U.S. application Ser. No. 12/877,560 entitled Devices, Systems and Methods for Field of View Control Imaging Systems, each of which is herein incorporated by reference in its entirety.

In one exemplary embodiment, the imaging system 10 utilizes the B-mode module 755 to perform B-mode imaging on the forward sweep or scan, and utilizes the F-mode module 760 to perform F-mode imaging on the return sweep or scan. This embodiment may utilize any swept single-element imaging system where only a portion of the total scan is presently utilized for image acquisition. For example, the current FLUD imaging system scans only on the forward scan and achieves a frame rate of 20 frames per second (FPS). If the currently unused return scan were used for F-Mode imaging, the display frame rate would remain at 20 FPS.

In another exemplary embodiment, the acquired data used to generate grayscale B-Mode imaging by the B-mode module 755 can be processed for F-Mode imaging by the F-mode module 760 in parallel, allowing for substantially simultaneous B-Mode and F-Mode imaging. In this embodiment the B-Mode and the F-Mode pulse can be the same. Depending on the methods used for B-Mode imaging, this may present tradeoffs such as sacrificing the depth of penetration and/or axial resolution to achieve usable color flow information.

In yet another exemplary embodiment, the B-mode module 775 and the F-mode module 760 cooperate to build the hybrid color flow image 720 by a method of line interleaving. If the transducer 108 is swept slowly enough, it is possible to interleave B-mode and F-mode lines without a strong affect on image quality. As the sweep time slows, adjacent lines are placed closer together. If the sweep time is slow enough, it is possible to group F-mode imaging between B-mode lines without sacrificing B-mode line density to the point of an unacceptable lateral resolution. Although the method of line interleaving produces the highest frame rate of the aforementioned methods, the method produces reduced spatial sampling density, and consequently reduced spatial resolution, for both B-mode and F-mode imaging modalities. The reduced sampling rate per F-mode line may also have the negative effect of increasing aliasing in the velocity estimation.

As shown in FIG. 15, which illustrates an example of B-mode and F-mode imaging through line interleaving, the different line modalities may be interleaved at variable rates to improve the spatial sampling density of one modality at the expense of the other. In FIG. 15, the imaging system 10 is configured to weigh the B-mode spatial quality above the F-mode spatial quality, a condition which is reflected by the presence of two B-mode lines 815 interleaved between each F-mode line 820.

The acquisition controller 750 may also be programmed to acquire F-mode acoustic samples to a depth that is less than that for the B-mode acoustic samples in line interleave or frame interleave acquisition modes. Reducing the F-mode depth, if appropriate for a particular application, may decrease F-mode aliasing. In one example, if B-mode samples are taken to a depth of 50 mm, then F-mode samples may be taken to a depth of 25 mm. The time of flight for each pulse in the F-mode is approximately one half as long as the time of flight in the B-mode. As will be appreciated, if F-mode depth is decreased a greater number of samples may be taken within a defined period thereby increasing the line density and the pulse repetition frequency in the F-mode. Greater pulse repetition frequency can increase measurable velocities. In addition, with increased line density, larger flow groups may be used since the first and last member of the flow group are more tightly correlated. In instances of line interleaving, decreasing F-Mode depth may also improve spatial resolution for both imaging modalities as well.

Returning to FIG. 12, the scan converters 775, 790 translate the acoustic samples from an angular or polar coordinate system to a Cartesian coordinate system for display on the monitor 400 using a common raster format.

The scan converter 790 uses the measured or expected angular position for each F-mode line to translate the data set to a Cartesian coordinate system. In addition, the angular velocity for each F-mode line is known and may be used. The B-mode and F-mode scan converters 775, 790 convert to the equivalent output physical space to ensure alignment of the overlaid modalities.

In the pictured embodiment, the imaging compositor 765 creates the hybrid flow image 720 by selecting B-mode or F-mode pixels based on B-mode intensity and/or pre-established minimum velocity thresholds. As the rotating imaging core 110 and transducer 108 rotate within the sheath 120, the imaging compositor 765 builds an image of the artery 600 (commonly referred to as a B-scan) from the succession of A-lines from the grayscale analyzer 770 and the velocity computer 785. The echo amplitude and velocity data are combined into color-coded A-lines and scan converted in the scan converters 775, 790 for display as the hybrid flow image 720 on the color monitor 400.

The image compositor 765 may perform a variety of functions, including grayscale mapping (e.g., log compression, gamma correction, etc.) to transform the wide dynamic range amplitude data into display brightness in a format that is pleasing to the eye and easy to interpret, scan conversion to transform the polar scanning format of the IVUS catheter 100 into a raster format for compatibility with the color monitor 400, and combination of the grayscale and velocity data into a hybrid color flow image format. There are a number of schemes known to those skilled in the art for combining the gray-scale IVUS data with the corresponding velocity data or information to produce a hybrid flow image. One simple scheme is to establish a threshold for the maximum likely tissue velocity, and then to assume that any velocity greater than this threshold must represent moving blood.

In some embodiments, a negative threshold and a positive threshold may be used, wherein any velocity below the negative threshold is assumed to retrograde flow, any velocity above the positive threshold is assume to be antegrade flow, and any velocity between the positive and negative thresholds is assumed to be stationary or slow-moving tissue. This velocity threshold scheme can be used to generate a simple, three level color mask, with blue tint applied to the grayscale value for any velocity below the negative threshold, red tint for any velocity above the positive threshold, and no tint (grey) for any velocity values between these threshold values representing stationary or slow-moving tissue. In other embodiments, the color flow imaging may use the mask to define the vessel boundaries and support border detection, virtual histology, or a de-speckling algorithm to more clearly distinguish the blood from the stationary tissue.

In some embodiments, the velocity threshold may be chosen to separate moving blood with axial velocities in the 100 to 200 centimeters per second (cm/sec) range from moving tissue with typical velocities on the order of 3 cm/sec or less.

In some embodiments, a more elaborate scheme may be used with shades of red through yellow encoding positive velocities, with shades of blue through green encoding a range of negative velocities, and with stationary and slow moving tissue receiving a neutral (grey) tint.

Another option might be to forego the color display entirely, and simply use the velocity information to identify moving blood, and then to suppress the grayscale brightness of the blood speckle to more clearly differentiate the moving blood from the stationary or slow-moving vessel wall. Advanced algorithms might even integrate the velocity map over the cross-section of the artery to provide a quantitative measurement of volumetric flow in the artery.

The echo amplitude and velocity data or information may be independently presented as separate images of echo amplitude and Doppler velocity over the field of view, but, in some embodiments, it is preferred to combine these two sets of data or information into the hybrid flow image 720 (shown in FIG. 8) combining the grayscale IVUS image with the velocity data encoded as shades of red and blue (for antegrade and retrograde flow, respectively), with stationary and slow-moving tissues displayed in shades of grey. Furthermore, the combined echo amplitude and velocity data can be further analyzed to extract anatomic features of the vessel 600 (shown in FIG. 5) such as the lumen border or functional measures such as volumetric flow. Such added analyses, facilitated by the availability of the combined echo amplitude and velocity data, further enhance the value of the imaging system 10.

In particular, the combined echo amplitude and velocity data may be utilized by the imaging system 10, for example but without limitation, to enhance suppression of blood echoes, luminal border and cross-sectional area detection, quantitative blood flow measurements, and thrombus detection. The imaging system 10 may enhance the contrast between the blood echoes and the vessel wall by using color to highlight the moving blood or by simply deemphasizing the moving blood by simply reducing the brightness of the fast-moving blood. For example, to suppress blood echoes from the final image 720, the imaging system 10 may hide the echoes that contain a significant velocity component so that the vessel lumen 603 (shown in FIG. 5) appears empty or darker than normal (as represented by the moving blood representation 723 in the image 720), thereby enhancing the distinction between the luminal blood and the vessel wall.

To enhance luminal border detection, the imaging system 10 uses the velocity data to improve the algorithm for automatic (computer-based) detection of the lumen border and the lumen cross-sectional area. These can be determined by manually tracing the lumen borders or by placing markers at intervals around the vessel border, but it is highly advantageous if those measurements are automatically provided by a computer algorithm that identifies the border on its own. Some IVUS imaging systems include such automated measurement algorithms, but these frequently require human intervention to improve the quality of the border detection. Providing velocity information to the automatic border detection algorithm can improve the quality of the result and reduce the need for tedious manual tracing of the borders.

As described above, in a traditional IVUS imaging system, the differentiation between moving blood and stationary thrombus may be very subtle. There may a slight difference in the temporal appearance of the speckle pattern, but there is often very little difference in the echogenicity of blood versus thrombus (particularly fresh thrombus). However, velocity provides a very strong signature to differentiate moving blood from stationary thrombus, and flow imaging by the imaging system 10 utilizing echo velocity data may greatly improve the detection of thrombus.

To enhance determinations of quantitative blood flow, the imaging system 10 can numerically integrate the echo velocity data over the cross-sectional area of the vessel lumen 603 to provide a quantitative measurement of volumetric blood flow within the artery 600 (shown in FIG. 5). The combination of grayscale IVUS imaging with echo velocity measurement makes it possible to accurately quantify blood flow. Blood flow calculation provides functional parameters to supplement the anatomic measurements provided by the hybrid flow image 720 (shown in FIG. 8). By comparing the blood flow under hyperemic and resting conditions, the coronary flow reserve can be computed as the ratio of the two flows to provide an important figure of merit for cardiac performance. The use of a pharmacologic agent, such as, by way of non-limiting example, adenosine, to stimulate maximum hyperemia in the vessel 600 may facilitate the calculation of coronary flow reserve, an important diagnostic value.

For application in coronary IVUS imaging, the echo velocity data is important for its role in helping to differentiate blood from tissue. The anatomy and physiology of the coronary arteries creates unique blood flow characteristics. In the coronary arteries, blood flow occurs predominantly during the diastolic phase of the cardiac cycle, during which tissue motion is at a minimum because the heart muscle is relaxed. In some instances, early diastole is a preferred phase of the cardiac cycle in which to use the blood velocity to assist with border detection. During early diastole, the velocity information provides maximum differentiation between the stationary tissue and the moving blood, since blood velocity is at its maximum and the heart motion is minimal.

Diastole is also a preferred time for measuring the artery cross-sectional area and diameter, while the distortion of the lumen due to compression of the heart muscle is minimized. In general, it is advantageous to use electrocardiogram (ECG) gating to identify the diastolic phase, and to select diastolic frames of the hybrid flow IVUS image for detailed quantitative analysis.

In the peripheral arteries, however, where flow occurs predominantly during systole and where tissue motion is less significant, systolic gated frames may be more appropriate for detailed quantitative analysis.

In color flow imaging applications throughout most parts of the body (e.g., but not by way of limitation, hepatic, carotid, or peripheral artery), the tissue motion is negligible, so the velocity threshold for classification of an echo as a moving blood echo can be very low. In the case of coronary imaging, however, the tissue motion can be quite prominent because the coronary vessels overlie the heart muscle, thereby making it more difficult to distinguish tissue motion from blood flow. Although the motion of the heart muscle is quite rapid during early systole when the ventricles rapidly contract, the elongate member 100 tends to move with the heart by virtue of its position within the coronary artery. Thus, the relative motion between the catheter and the surrounding tissue is usually significantly less than the absolute motion of the heart.

In another embodiment, the system utilizes a B-Mode mux to combine the B-Mode and F-Mode data. In this embodiment, if the energy of the B-Mode data is substantially higher than the average energy acquired from the F-Mode processing, then the B-Mode data will be displayed.

An example of a fast movement of the catheter 100 with respect to the heart would be for the catheter to shift one vessel diameter (approximately 3 millimeters) during the approximately 100 milliseconds that constitutes the early portion of systole. The corresponding relative tissue velocity in this case would be approximately 3 centimeters per second. Throughout most of the cardiac cycle, and in the majority of locations throughout the epicardial arterial tree, the actual tissue velocity will be much less than this maximum likely tissue velocity estimate. Thus, for this additional reason, it may be beneficial to obtain a diastolic gated flow measurement to more accurately obtain blood flow velocities.

In addition, the principles of the above described imaging system and methods can be applied to other forms of imaging systems with moveable energy emitters such as transducers and mirrors. More specifically, while the above disclosure discusses application of the concepts to transducers or energy emitters that oscillate, it will be understood that the same methods can be applied to energy emitters that rotate 360° in a single direction. Still further, while the description above is set forth in relation to use of an ultrasound transducer, other forms of energy emitters such lasers or light sources may be controlled to take advantage of the systems and methods described above.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intravascular ultrasound (IVUS) imaging system, the system comprising:
   an ultrasound emitter and receiver movably disposed within an IVUS imaging device comprising an elongate member sized and shaped to be positioned in a lumen of a blood vessel of a patient;
   an actuator coupled to the emitter, the actuator moving the emitter through a path comprising at least a portion of an arc within the blood vessel of the patient, wherein the actuator is configured to oscillate the emitter about a pivot pin such that the emitter sweeps forward and returns along the at least a portion of an arc within a plane perpendicular to an axis of the pivot pin; and
   a control system in communication with the actuator such that the control system controls movement of the emitter through the path at a desired angular velocity profile, wherein the desired angular velocity profile comprises an angular velocity of the emitter that is non-linear over time so that the emitter moves at a first velocity during the forward sweep of the arc and at a second velocity that is different than the first velocity during the return sweep of the arc, wherein the first velocity is associated with F-mode ultrasonic imaging and the second velocity is associated with B-mode ultrasonic imaging, wherein the control system includes:
   an acquisition controller controlling the emission of pulses from the emitter including a plurality of F-mode pulses emitted during the forward sweep at the first velocity and a plurality of B-mode pulses emitted during the return sweep at the second velocity, and receiving, from the receiver, echo velocity acoustic samples from the F-mode pulses and echo amplitude acoustic samples from the B-mode pulses associated with the pulses emitted along the forward and return sweeps of the emitter, respectively;
   an intensity module processing the echo amplitude acoustic samples to generate echo amplitude data, wherein the intensity module compares the echo amplitude acoustic samples to a variable echo amplitude acoustic threshold, wherein the variable echo amplitude acoustic threshold is adjusted based upon the angular velocity of the emitter;

a flow module processing the echo velocity acoustic samples to generate echo velocity data; and an image compositor generating a hybrid IVUS image representing both of the echo amplitude data e-and the echo velocity data in the same image, wherein the IVUS image represents the echo amplitude data in grayscale and the echo velocity data in color;

wherein the acquisition controller further controls the ultrasound emitter and receiver to obtain the echo velocity data associated with ultrasound reflections of the first pulses from a first depth within the blood vessel including the lumen and to obtain the echo amplitude data associated with ultrasound reflections of the second pulses from a second depth within the blood vessel including a lumen boundary, the first and second depths located along a ray of the first and second pulses respectively from the emitter positioned within the lumen of the blood vessel, wherein the second depth is greater than the first depth.

2. The system of claim 1, wherein the actuator is disposed within the elongate member.

3. The system of claim 2, wherein the actuator rotates the ultrasound emitter through only a portion of an arc such that the ultrasound emitter oscillates between a first point and a second point along the path.

4. The system of claim 3, wherein the control system processes the echo amplitude data as the emitter moves from the first point to the second point, and processes the echo velocity data as the emitter moves from the second point to the first point.

5. The system of claim 1, wherein the ultrasound emitter comprises a transducer operable at 10 to 20 MHz.

6. The system of claim 1, wherein the image includes a simultaneous graphic representation of both the echo amplitude data and the echo velocity data.

7. The system of claim 6, wherein the graphic representation includes a color representation of the echo velocity data.

8. The system of claim 6, wherein the graphic representation includes a grayscale representation of the echo velocity data.

9. The system of claim 1, wherein the control system processes the echo amplitude data and the echo velocity data in an alternating series fashion by processing the echo amplitude data for a first frame and processing the echo velocity data for a second frame.

10. The system of claim 1, wherein the control system processes the echo amplitude data and the echo velocity data in an interleaved series fashion by processing one of the echo amplitude data and the echo velocity data for each pulse within a frame at a variable rate proportionate to the angular velocity of the emitter.

11. The system of claim 1, wherein the control system processes the echo amplitude data and the echo velocity data in a parallel fashion by processing the echo amplitude data for each first pulse and the echo velocity data for each second pulse simultaneously within a frame.

12. The system of claim 1, wherein the control system further defines the vessel borders based on both the echo amplitude data and the echo velocity data.

* * * * *